United States Patent [19]

Sommer et al.

[11] 4,006,189
[45] Feb. 1, 1977

[54] PROCESS FOR PURIFYING GLYOXAL

[75] Inventors: August Sommer, Herne; Richard Wessendorf, Essen-Heisingen, both of Germany

[73] Assignee: Veba Chemie AG, Gelsenkirchen-Buer, Germany

[22] Filed: June 11, 1974

[21] Appl. No.: 478,431

[30] Foreign Application Priority Data

June 13, 1973 Germany .......................... 2329957

[52] U.S. Cl. ........................................... 260/601 R
[51] Int. Cl.$^2$ ......................................... C07C 47/02
[58] Field of Search ................................ 260/601 R

[56] References Cited

UNITED STATES PATENTS 2,246,049  6/1941  Lange ............................ 260/601 R
3,367,973  2/1968  Schramm et al. ............... 260/601 R

FOREIGN PATENTS OR APPLICATIONS 2,159,975  6/1973  Germany ....................... 260/601 R

*Primary Examiner*—Donald G. Daus
*Assistant Examiner*—D. B. Springer
*Attorney, Agent, or Firm*—Burgess, Dinklage & Sprung

[57] ABSTRACT

Crude glyoxal solutions obtained for example by the oxidation of acetaldehyde with nitric acid are purified by removing volatile acids followed by neutralization. Thereafter, the glyoxal is converted into a glyoxal glyoxal-di-(alkylhemiacetal) with an alcohol containing 1 to 3 carbon atoms with water removal during the conversion. After separating salts and other impurities, the glyoxal-di-(alkylhemiacetal) is hydrolyzed with water at elevated temperatures to yield pure glyoxal hydrate.

6 Claims, No Drawings

PROCESS FOR PURIFYING GLYOXAL

BACKGROUND

This invention relates to a process for the purification of glyoxal via the preparation of commercial crude glyoxal solutions to pure, aqueous glyoxal solutions.

Glyoxal is commercially prepared by oxidation of acetaldehyde with aqueous nitric acid. The raw product obtained thereby contains unreacted starting materials, acetaldehyde and nitric acid and a number of byproducts, all of which renders complete separation considerably difficult.

Byproducts included acids volatile at elevated temperatures, for example acetic acid and formic acid, non-volatile acids, for example glyoxal acid, glycolic acid and oxalic acid and organic electrolyte and other impurities. These cause a more or less heavy discoloration of the product.

The main part of the volatile acids, however, can be removed by distillation and concentration of the solution, but there is obtained a crude glyoxal which still contains residual acid which cannot be removed by this method. According to prior methods, these acids are neutralized with carbonates of a metal of Group II, especially calcium carbonate. The separation of calcium salts in solid form is, however, incomplete, so that the glyoxal solution also contains calcium ions. Glyoxal solutions purified in this way have a dark yellow color.

It has been proposed to remove the non-volatile acids with anion exchangers, for example according to the method of German Patent 1,154,081. A comparison of the acid content of glyoxal solutions purified by distillation with the capacities of an anion exchanger (~1,5 val/l) shows that the same volume of the exchanger resin is required for the deacidification of a certain volume of 40% crude glyoxal solution. With an anion exchanger resin, both after saturation to remove the glyoxal solution and after regeneration with soda lye, a 6- to 10-fold volume of purification liquid is needed which makes the efficiency of this process very poor.

A drawback to the electrolytical dialysis process is also the high water use which is described in German Patent 1,618,283. At a residence time of 20 hours, a glyoxal output of 80 to 90% is reached.

According to the process of Russian Patent 168,670, at the tetraacetal is produced from the crude glyoxal and ethanol and is then hydrolyzed after purification by distillation with acid cation exchangers. According to experiments and information in the literature (J.A.C.S. 77, 1285 (1955)), however, the formation of acetal even with excess alcohol takes place in a very unsatisfactory manner.

According to another process, described in German Offenlegungsschrift 2,159,975, the production and use of glyoxal hemiacetals as an intermediate product for producing of acid-free, aqueous glyoxal solutions is described. Glyoxal demiacetals are isolated from technical glyoxal solutions and purified by reaction with water immiscible alcohols. In a three-stage hydrolysis with boiling water only 80% as hydrate can be achieved. The solution still contains large traces of the immiscible alcohol. A drawback to this process is the incomplete separation of the glyoxal from its solution which cannot be corrected by using an excess of the immiscible alcohol.

SUMMARY

Surprisingly, it was found that for the purification of glyoxal, the glyoxal di-(alkylhemiacetal) can be formed by the reaction of the glyoxal with alcohols containing 1–3 carbon atoms.

This invention thus provides a process for the purification of glyoxal solutions, especially those obtained by the oxidation of acetaldehyde with nitric acid. The crude glyoxal solution is freed of volatile acids and neutralized. The glyoxal is converted with an alcohol containing 1 to 3 C-atoms with water separation into the glyoxal di-(alkylhemiacetal). After separation of the salts and other impurities, the glyoxal-di-(alkylhemiacetal) is hydrolyzed with water at increased temperature to yield pure glyoxal hydrate.

DESCRIPTION

The reaction of glyoxal hydrate with alcohols in a molar ratio of 1:2 in the absence of heavy acids leads to the formation of glyoxal di-(alkylhemiacetal), if the water is removed while formation of the glyoxal-di-(alkylhemiacetal) takes place, to wit:

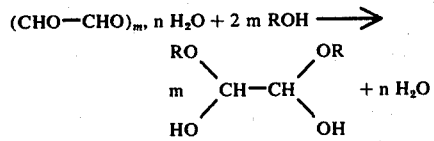

The glyoxal-di-(alkylhemiacetal) is advantageously formed using alkanols with 1–3 C-atoms such as methanol, ethanol, isopropanol and n-propanol for the purification of acid crude glyoxal. The glyoxal-di-(alkylhemiacetal) is easy to produce, purify and convert, that is, by heating with excess water, it is reformed into glyoxal hydrate and the alcohol, to wit:

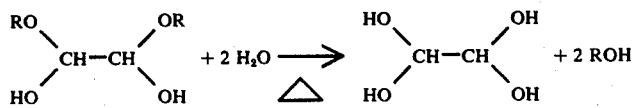

R is the above reaction schemes is a $C_{1-3}$ alkyl group. The process of the invention also involves the separation of non-volatile acids from the crude glyoxal solution. The salts of these acids are made by neutralizing the acids with aqueous alkali, such as sodium carbonate, sodium hydrogen carbonate or soda lye and the corresponding potassium compounds. The pH-value of the solution should remain in the acid range since glyoxal is converted in the presence of alkali according to the Cannizzarro-reaction into glycolic acid. With the formation of glyoxal di-(alkylhemiacetal), the acid salts drop out and can be separated according to known methods. A preferred method is to remove the water during the reaction only to the extent that the salts and other impurities remain in solution and can be separated as the lower liquid phase.

In order to further decrease the solubility of the separating acid salts in the glyoxal demiacetal, the glyoxal demiacetal can be diluted with a solvent immiscible in water, as for example benzene or benzine, and this solution can be purified, if needed. For this purpose, a 10 to 40% neutral, aqueous glyoxal solution is advantageously used which absorbs the still existing salts and can be separated as the lower phase. With this process, it has been surprisingly found that unknown substances, which cause decolorations, are removed in this way.

The invention will be further described with reference to the following examples which are intended to illustrate the invention without limiting same in any manner.

EXAMPLE 1

200 g of a crude glyoxal solution (glyoxal content 16.2%, acid number 176 (mgKOH/g)) were evaporated in a rotary evaporator (vac. 30 Torr. bath temperature 70° C) down to a residual solution of 61 g (glyoxal content 53%, acid number 138).

To this solution a suspension of sodium hydrogen carbonate (about 11 g) was gradually added after cooling while stirring in water until a pH-value of 5.1 was measured.

The solution was evaporated in a rotary evaporator until dry and afterwards the residue treated with 100 ml absolute ethanol under stirring at 65% C. After cooling, 200 ml of dry ether was added to the formed solution and after addition of some Celite $^R$ (Bayer) it was filtered from the salts that dropped out. The residue was treated once more with 50 ml hot ethanol and again filtered.

From the combined filtrates, the ether was distilled off. Adding water drop by drop the alcohol which had formed by hydrolysis was taken off employing a vacuum whereby 38.8 gms. glyoxal hydrate (80.8% pure) was obtained as residue.

This corresponds to a yield of 94.5% of the theory.

EXAMPLE 2

300 g of a commercial glyoxal solution (glyoxal content 15%, acid number = 160 ) were treated in a rotary evaporator in the vacuum of about 30 Torr, so that a 50% glyoxal solution with an acid number of 126 (mgKOH/g) remained. To this solution an aqueous suspension of sodium hydrogen carbonate was added while stirring until a pH-value of 5.1 was measured. Afterwards the solution was further evaporated until the formation of solid glyoxal hydrate began. Then 200 g isopropylalcohol was added to the residue and stirred 30 minutes at 70° C until the formation of bis-di-(alkyl-hemiacetal). In order to complete the separation of the salts, the reaction mixture was dehydrated by azeotropic distillation while further dry isopropyl alcohol dropped into the reaction mixture until a water content of < 0.1% was determined in the distillate.

After cooling the precipitate could be separated by filtration.

To the filtrate 50 ml H$_2$O was added. This mixture was heated at a reduced pressure while additional water drops were added whereby all isopropanol was distilled off.

As residue 135 g 30% glyoxal solution remained being yellow colored and having an acid number of 3 mgKOH/g.

EXAMPLE 3

A crude glyoxal solution was liberated in the rotational evaporizer of volatile acid and afterward adjusted with 30% soda lye to the pH-value 6.0.

The solution contained 33.1% glyoxal and was colored heavily yellow.

176 g (1 mol glyoxal) of this solution was stirred with 120 g isopropanol and 120 g benzene in a three-necked flask and heated up to boiling. From the condensed vapors, 32 gms. of water was separated. After cooling the upper phase which only was slight colored and turbid was separated. After twice washing with 15 ml of a 20% glyoxal solution each, a completely clear, nearly colorless solution was formed.

To the solution, 50 ml. of water was added. The mixture was heated in the rotational vaporizer whereby water was dropped in. As a residue 172 g of a glyoxal solution remained which had a glyoxal content of 28.9% and an acid number of 0.8 (mgKOH/g).

In order to remove slight sodium traces a sample of this solution was treated with dry cation exchanger Lewatit S 100 $^R$. Thereby an acid number of 1.3 mg KOH/g resulted which corresponds to a 4.5 mg KOH/g glyoxal.

The salt-bearing, brown colored residue was treated twice with isopropanol/benzene, whereby the total of 6.3 g glyoxal were received.

Subsequently the residue was dissolved in water. It still contained 1.6 g glyoxal.

The overall yield amounted to 56 g glyoxal, which corresponds to 94.8% of the theory.

EXAMPLE 4

The purification of the glyoxal was carried out according to Example 3, the separated upper phase, however, was not washed.

At a yield of 94% of the theory, a glyoxal solution was obtained whose acid number was also amounting to 0.8 (mgKOH/g).

After the cation exchange with Lewatit S 100$^{(R)}$ an acid number of 8.6 mg KOH/g glyoxal, however, was measured.

What is claimed is:

1. In a process for the recovery of an aqueous solution of purified glyoxal hydrate from a mixture of glyoxal, volatile acids and non-volatile acids wherein said mixture is subjected to distillation to remove said volatile acids to leave behind a residue of said glyoxal and said non-volatile acids and to said residue there is added an alkali to neutralize said non-volatile ile acids and convert them to the corresponding alkali salt, the improvement for recovering a purified aqueous solution of glyoxal hydrate which comprises the steps of:
   A. Contacting the resultant mixture following addition of said alkali with a C$_1$-C$_3$ alcohol while maintaining the pH of the resultant solution in the acid range and removing liberated water by distillation;
   B. Removing alkali salts of said non-volatile acids leaving behind glyoxal-di-(alkyl hemiacetal);
   C. Contacting said glyoxal-di-(alkyl hemiacetal) with water under neutral hydrolysis conditions; and
   D. recovering an aqueous solution of glyoxal hydrate.

2. A process according to claim 1 wherein the amount of water removed in step A is only to the extent that said alkali salts of non-volatile acids remain in aqueous solution whereby forming an upper liquid organic phase containing said glyoxal-di-(alkyl hemiacetal) and a lower liquid phase containing water and said salts of non-volatile acids and said lower liquid phase is separated from said upper liquid phase.

3. A process according to claim 1 wherein said water is removed until said salts of non-volatile acids are precipitated and thereafter said precipitated salts are separated from said glyoxal-di-(alkyl hemiacetal) compound.

4. A process according to claim 1 wherein prior to step B ans subsequent to step A there is added to the product of step A benzene or benzine and to the resultant mixture there is added an aqueous glyoxal solution whereby there is formed an upper organic liquid phase containing glyoxal-di-(alkyl hemiacetal) and a lower liquid phase comprising water and the salts of non-volatile acids and, according to step B, said alkali salts of non-volatile acids are separated from glyoxal-di-(alkyl hemiacetal) by separating the phases.

5. A process according to claim 1 wherein step C is carried out by a process consisting essentially of contacting said glyoxal-di-(alkyl hemiacetal) with water.

6. A process for the recovery of an aqueous solution of purified glyoxal hydrate from a mixture of glyoxal, volatile acids and non-volatile acids which comprises the steps of:
A. Subjecting said mixture to distillation to remove said volatile acids to leave behind a residue of said glyoxal and said non-volatile acids;
B. Adding to said residue sufficient alkali to neutralize said non-volatile acids to convert them to their corresponding alkali salts;
C. Contacting the resultant mixture with a $C_1$–$C_3$ alcohol while the pH of the resultant mixture is maintained in the acid range and removing liberated water by distillation;
D. Removing alkali salts of said non-volatile acids from the product of the preceeding step thereby leaving behind glyoxal-di-(alkyl hemiacetal);
E. Contacting said glyoxal-di-(alkyl hemiacetal) with water under neutral hydrolysis conditions; and
F. Recovering an aqueous solution of glyoxal hydrate substantially free of volatile and non-volatile acids.

* * * * *

UNITED STATES PATENT OFFICE
CERTIFICATE OF CORRECTION

Patent No. 4,006,189  Dated February 1, 1977

Inventor(s) August Sommer et al.

It is certified that error appears in the above-identified patent and that said Letters Patent are hereby corrected as shown below:

Column 1, line 12, "byproducts" should read -- by-products --.

1, line 14, "Byproducts" should read -- By-products --.

Column 2, line 31, in the formula, "$(CHO-CHO)_m$, n $H_2O$" should should read -- $(CHO - CHO)_m \cdot n\ H_2O$ --.

Column 3, line 28, "65%C" should read -- 65°C --.

Column 4, line 51, after "non-volatile", delete "ile".

Signed and Sealed this twelfth Day of July 1977

[SEAL]

Attest:

RUTH C. MASON
*Attesting Officer*

C. MARSHALL DANN
*Commissioner of Patents and Trademarks*